United States Patent
Ishizaka et al.

[11] Patent Number: 5,336,271
[45] Date of Patent: Aug. 9, 1994

[54] METHOD FOR INCREASING THE PROPORTION OF A CRYSTALLINE ORGANIC COMPOUND WHICH REMAINS UNCRYSTALLIZED IN A COMPOSITE PARTICULATE PRODUCT AND SUPPRESSING RECRYSTALLIZATION

[75] Inventors: Takafumi Ishizaka; Yuji Kikuchi, both of Tokyo; Masumi Koishi, Sagamihara, all of Japan

[73] Assignee: Nara Machinery Co., Ltd., Tokyo, Japan

[21] Appl. No.: 854,840

[22] Filed: Mar. 20, 1992

[30] Foreign Application Priority Data

Mar. 26, 1991 [JP] Japan ................... 3-086332

[51] Int. Cl.$^5$ ............................................. B01J 8/00
[52] U.S. Cl. ............................ 23/293 R; 241/16; 241/27; 514/160; 514/404; 514/420; 514/568; 514/570; 514/625
[58] Field of Search ............... 241/16, 27; 23/293 R; 514/570, 420, 625, 404, 160, 568

[56] References Cited

U.S. PATENT DOCUMENTS

| 3,688,991 | 9/1972 | Andrews | 241/27 |
| 3,713,593 | 1/1973 | Morris et al. | 241/27 |
| 4,298,399 | 11/1981 | Formica et al. | 241/16 |

FOREIGN PATENT DOCUMENTS

| 641298 | 5/1962 | Canada | 241/16 |
| 102883 | 9/1978 | Japan | 241/16 |
| 298366 | 12/1990 | Japan | 241/16 |

*Primary Examiner*—Wayne Langel
*Attorney, Agent, or Firm*—Jacobson, Price, Holman & Stern

[57] ABSTRACT

A method for increasing the proportion of a crystalline organic compound which remains amorphous and suppressing recrystallization in which a crystalline organic compound and a hydrophilic polymer substance are fixed onto a surface of core particles by means of impacts applied in a high velocity gas stream. The solubility and stability of the resulting composite product, such as a drug for internal use, can be improved.

14 Claims, 5 Drawing Sheets

PRODUCT (A)        PRODUCT (D)

PRODUCT (A)        PRODUCT (D)

METHOD FOR INCREASING THE PROPORTION OF A CRYSTALLINE ORGANIC COMPOUND WHICH REMAINS UNCRYSTALLIZED IN A COMPOSITE PARTICULATE PRODUCT AND SUPPRESSING RECRYSTALLIZATION

FIELD OF THE INVENTION AND RELATED ART STATEMENT

The present invention relates to a method for increasing the proportion of the material which is amorphous in a product made of a crystalline organic compound and for suppressing recrystallization thereof. More specifically, the present invention relates to a method for increasing the proportion of the organic crystalline compound which is amorphous in a composite particulate or granular product of a crystalline organic compound and for suppressing recrystallization thereof, which comprises formation of a fixed layer of amorphous state from said at least one crystalline organic compound and a hydrophilic polymer substance over the surface of a core particle by means of impact application in a high velocity gas stream.

In the manufacture of pharmaceutical products in solid form, powdery medical materials, such as drugs and excipients, have been manufactured by a wet method. For example, granulation has been done by a fluidized bed technique or by a powder mixing technique, wherein the starting pulverized product has to have a particle size of at least several tens of micrometers. The processing with pulverized products of finer sizes has been impossible with these methods. Therefore, in order to manufacture products with better performance and higher quality, an urgent need has been recognized for establishing an improved pharmaceutical manufacturing technique which makes it possible to design drugs based on a new point of view and process powders of finer particle sizes.

Under these circumstances, there has been developed a dry process for producing composite granulated products by making use of impact application in a high velocity gas stream. This method requires no organic solvent or water and makes it possible to produce composite granulated drug products in which medicinal components are held fixed on supporting particles of an excipient. It has been reported, for crystalline drugs in particular, that a mechano-chemical reaction takes place when mechanical impacts are given to the crystals of the drug by a technique of impact application in a high velocity gas stream, whereby a part of the crystalline medicinal product is converted into a an amorphous state and fused and fixed onto the surface of the supporting particle. Various advantages, such as improved ease of dissolving the product in the case of drugs which are not very soluble in water, have been reported.

However, since the composite state of a granular product may suffer from a temporal change depending on the intrinsic properties of each medicinal product, it has often been observed that the once formed amorphous portion of the composite product becomes, even though it is first formed as a laminated smooth layer and in an amorphous state, subjected to recrystallization during a long term storage, and even falls off from the supporting excipient particle in some cases. For medicinal products which are difficult to dissolve, so long as they are maintained in a composite form, the solubility of the products to water and the like can be improved irrespective of the crystalline state of the products. However, it has been difficult to maintain these products in such composite form and the amorphous state, even if the products are produced by the above-mentioned dry process.

OBJECT AND SUMMARY OF THE INVENTION

In consideration of these circumstances, it is an object of the present invention to provide an improved method for fixing a crystalline organic compound in an amorphous state on core particles, and further for maintaining the composite state between the crystalline organic compound and the core particles by inhibiting the recrystallization of the crystalline material by means of impacts applied in a high velocity gas stream.

The above object is achieved according to the present invention by fixing the crystalline organic compound and a hydrophilic polymer compound on the surface of the core particles by impact application in a high velocity gas stream, so as to increase the proportion of the compound which remain amorphous compared to the conventional dry processes for forming composite particles and suppress the change of the amorphous portion of the otherwise crystalline organic compound into a crystalline state.

In the method of the present invention, a crystalline organic compound is fixed onto the surface of core particles by the action of impacts effected in a high velocity gas stream, and a hydrophilic polymer compound is then fixed onto the surface of the crystalline organic compound, so as to form a solid solution in which the crystalline organic compound is mixed and dispersed into the hydrophilic polymer compound on a molecular level. This method allows the proportion of the crystalline organic compound which is in the amorphous state to increase compared with conventional dry methods for composite particle formation and suppress the alteration of crystal states in the product.

Also, according to another aspect of the present invention, a hydrophilic polymer compound is fixed onto the surface of core particles to form a layer by the action of impacts effected in a high velocity gas stream, and then the crystalline organic compound is fixed onto the surface of the hydrophilic polymer compound, so as to form a solid solution in which the crystalline organic compound is mixed and dispersed on the surface and inside of the layer of hydrophilic polymer compound on a molecular level. This method also allows the proportion of the crystalline organic compound which is in the amorphous state to increase compared with conventional dry methods for composite particle formation and suppress the alteration of crystal states in the product.

Further, according to still another aspect of the present invention, a crystalline organic compound and a hydrophilic polymer compound are simultaneously fixed onto the surface of core particles by the action of impacts effected in a high velocity gas stream, so as to form a solid solution in which the crystalline organic compound is mixed and dispersed in the layer of hydrophilic polymer compound on a molecular level. This method also allows the proportion of the crystalline organic compound which is in the amorphous state to increase compared with conventional dry methods for composite particle formation and suppress the alteration of crystal states in the product.

DETAILED DESCRIPTION OF PREFERRED EMBODIMENTS

Figure 1:
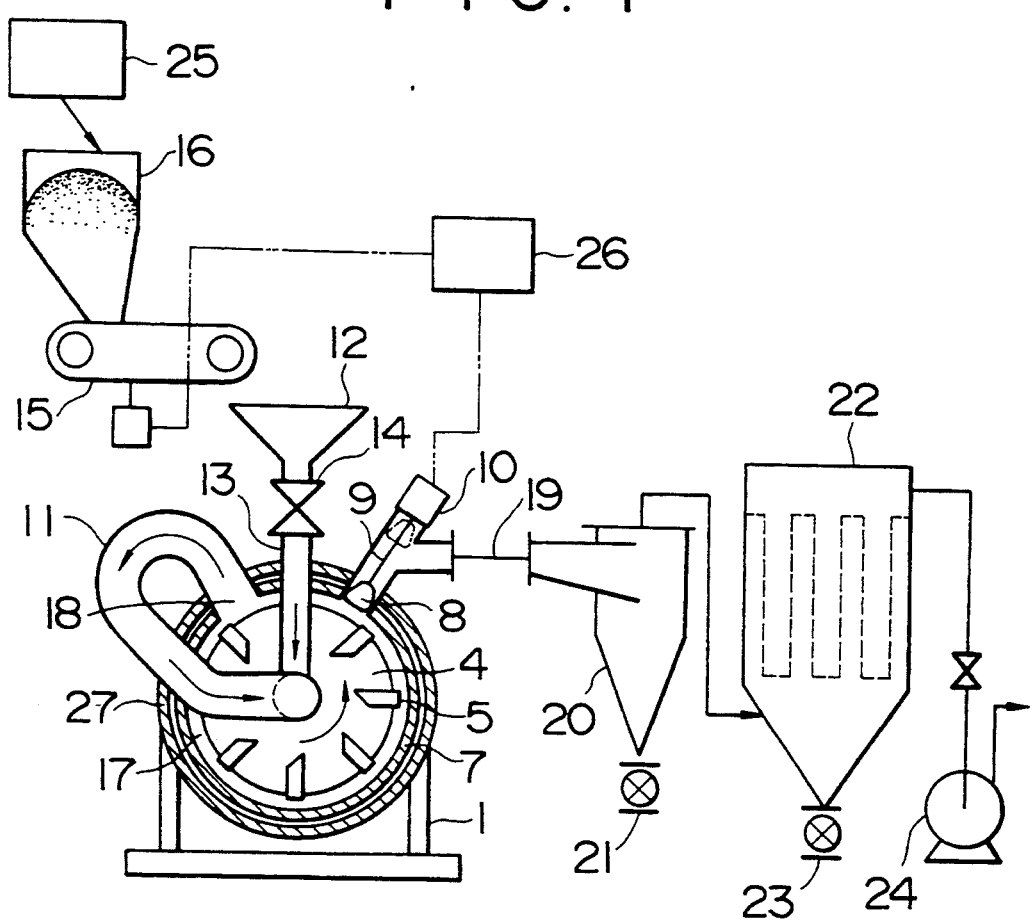
FIG. 1 is a schematic illustration of one embodiment of the process flow for realizing the method according to the present invention with a particle surface modifying device.

Below, the present invention will be described in more detail by way of example.

As a core particle on which the crystalline organic compound and the hydrophilic polymer substance are supported to form a composite particulate product according to the present invention, the following can be used for example: cellulose products to be used in various medicinal preparations, such as crystalline cellulose, hydroxypropyl cellulose, carboxymethyl cellulose and derivatives of them; starch, such as potato starch, corn starch, wheat starch, partially solubilized starch, dextrin and derivatives of them; sugars, such as milk sugar; and synthetic high polymeric materials, such as nylon, polyethylene, polystyrene. Use of inorganic substances may also be possible, for example, a powder of a metal, such as iron, nickel, aluminum, copper; metal oxides, such as alumina, zirconia; and carbides, such as silicon carbide.

Core particles having sizes in the range of from 0.5 micrometers to 1 mm are suitably employed. If the particle size of the core particle is less than 0.5 micrometers, the particles will drift in the gas stream and the mechanical impact will become difficult to be transferred to the particle. If, on the contrary, the particle size exceeds 1 mm, the particle tends to collapse by the mechanical impact and it becomes difficult to obtain the desired quality of the product. As for the shape of the core particle, sphere or ellipse is preferred, while any other shapes, such as lamella, needle and irregular forms, may also be permitted.

For a crystalline organic compound, or a medicament in particular, there may be enumerated, for example, ibuprofen, ketoprofen, flurbiprofen, indomethacin, phenacetin, oxyphenbutazone, ethenzamide, salicylamide, salicylic acid, benzoic acid and so on.

The particles of these crystalline compounds may be in any size, since they are subjected to a selective crushing in an impact chamber of a particle surface modifying device to be employed for realizing the method according to the present invention.

For a hydrophilic polymer substance, it is preferable to select a substance which easily forms a solid solution with the crystalline organic compound employed and which does not easily form a solid solution with the material of the core particle. Such a substance may be selected from, for example, polyethylene glycol, polyvinyl pyrrolidone, gelatine, hydroxypropyl cellulose and polyacrylamide.

EXAMPLES

In the following, the method according to the present invention is described by way of example of production of composite particulate products according to the present invention, in which a Japanese pharmacopoeial commercial corn starch product (abbreviated "CS") having an average particle size or dp 50 of about 15 micrometers, a commercial crystalline product of ibuprofen (an analgesic-antipyretic antiphlogistic drug; hereinafter referred to as "IP") and a commercial polyethylene glycol product PEG 6000 of Wako Pure Chemical Industries, Ltd.; referred to hereinafter as "PEG") are employed for the core particle, for the crystalline organic compound and for the hydrophilic polymer substance, respectively. Here, the commercial products, CS and IP, were used as such, while PEG was crushed as far as possible before its use with a jet mill (model TJ120 of Furointo Sangyo Kabushiki Kaisha).

Figure 2:
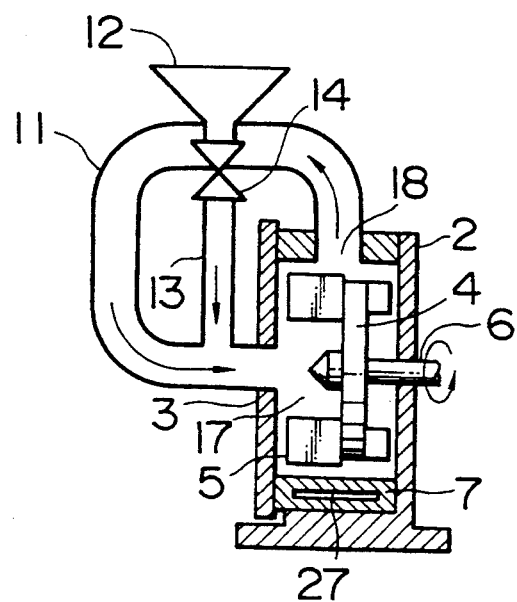
FIG. 2 is a schematic vertical sectional side view of the particle surface modifying device of FIG. 1.
Figure 3A:
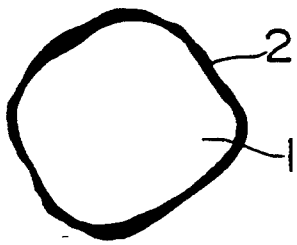
FIGS. 3(A), 3(B), 3(C) and 3(D) show four typical sectional structures of composite granules obtained according to the present invention.
Figure 3B:
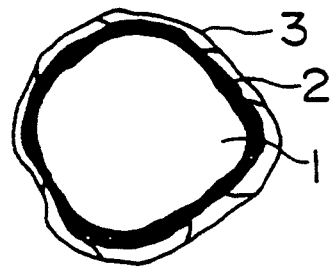
Figure 3C:
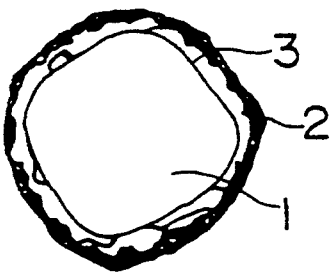
Figure 3D:
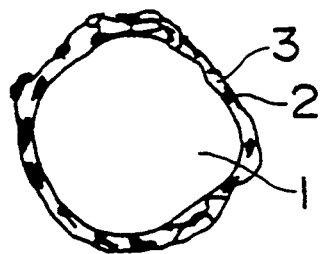

FIGS. 1 and 2 show the particle surface modifying device employed for producing the composite particulate product in these examples. This device has been developed for producing a functional composite particulate product in a dry manner with efficiency and with reduced production time by mechanically fixing small solid particles (called "child particles") onto the surface of core particles (called "parent particles") of size larger than the child particles and of material different from the child particles.

This apparatus comprises a casing 1, a rear cover plate 2, a front cover plate 3, a rotor 4 capable of rotating at a high rate of revolution and provided with a plurality of impact members 5 in a form of, in general, a hammer or blade, disposed radially over the rim of the rotor at a definite interval and a rotary shaft 6 pivotally supported in the rear cover plate 2, an impingement ring 7 arranged along and surrounding the outermost orbit of the impact members 5 at a distance thereto. The impingement ring 7 may have an irregular or flat inner face of voluntary shape. The distance between the outermost orbit of the impact members 5 and the inner face of the impingement ring 7 may, depending on the scale of the apparatus, preferably be in the range from 0.5 mm to 20 mm. The apparatus further comprises a valve 8 which has a valve stem 9 and an actuator 10 for operating the valve 8 and is disposed in the impingement ring 7 so as to fit closely to the exit opening for discharging the composite particulate product out of the apparatus, a circulation conduit 11 starting from an upper portion of the impingement ring 7 and terminating to the central opening of the front cover plate 3 to establish a circulation loop for the gas stream and the particles suspended therein, a supply means for the raw materials including a hopper 12 and a chute 13 connecting the hopper to the circulation conduit 11 via a valve 14, a metering feeder 15 for the raw materials connected to the raw stock storage reservoir 16. Inside the casing 1, an impact chamber 17 is demarcated between the rotor 4 and the surrounding walls. Reference numeral 18 indicates the starting opening of the circulation conduit 11.

The composite particulate product produced in the apparatus is discharged out of the apparatus via an exit line 19 into a cyclone 20, from which the composite particles separated are taken out via a rotary valve 21 at its bottom. The gas phase passed the cyclone enters into a bag filter 22, where the residual floating particles are collected and the so collected particles are taken out via a rotary valve 23 and the gas is exhausted to the atmosphere via a blower 24. In order to prepare for the case where the parent particle is to be covered preliminarily with the child particles, a known auxiliary preprocessor 25, such as, various kinds of mixers, automatic mortar or the like is provided before the hopper 16. The apparatus employed in this Example had been designed to effect an automatic batch-wise operation by a timing controller 26. Due to the complete batch-wise operation of the apparatus, the gas temperature within the apparatus may occasionally increase with time. By the arrangement of a jacket structure 27 for the impingement ring 7, such temperature elevation of the circulating gas stream can be suppressed and the temperature can be maintained at an adequate value by flowing a suitable coolant through the jacket 27.

The operation of the apparatus will be described in the following.

At the start, the valve 8 for discharging the particulate product, and the valve 14 for supplying the raw materials are kept closed, and the rotor 4 is actuated by a driving means (not shown) at a circumferential velocity of, for example, 80 m/sec. With the rotation of the impact members 5, an intensive flow of the internal air is caused. By the turbo effect due to the centrifugal force of the air stream, a circulation flow, namely a flow of completely self-enclosed circulation of air is produced passing from the opening 18 in the impingement ring 7 via the circulation conduit 11 and the central opening of the front cover plate 3 to the impact chamber 17. Here, the air flow rate is so high as compared with the total internal volume of the impact chamber 17 and of the circulation conduit, that an extremely large number of the air recirculation cycles will be repeated within a brief time. Thus, for example, when a rotor having an outer diameter of 118 mm is rotated at a circumferential velocity of 80 m/sec, a circulation flow at a rate of 0.48 m$^3$/min is realized and the number of the air recirculation cycles is calculated to be 774 per minute. The flow rate of the air circulation thus induced is proportional to the circumferential velocity of the rotor, so that the number of circulation cycles of the internal air becomes larger when the rotor speed increases.

For the purpose of the present invention, a rotor speed in terms of the circumferential velocity in the range from 30 to 150 m/see may be preferable. At a speed below 30 m/sec, a sufficient air flow will not be established in the gas circulation circuit, which causes an inefficient processing of the particulate product. On the other hand, a rotor circumferential velocity over 150 m/sec is difficultly attainable in ordinary technology.

Then, the valve 14 is opened to charge a powder mixture of the parent particles and the child particles heaped in the hopper 12 from the metering feeder 15 into the impact chamber 17 via the chute 13. After the last heap of the mixture has been introduced into the apparatus, the valve 14 is closed. If an automatic batch-wise operation is to be employed, the timing controller 26 is put into operation with a preset time requisite for the charging of raw stock determined preliminarily. The powder mixture is subjected to a mechanical impact in the impact chamber by the impact members 5 rotating at a high speed and the particles are scattered away to the surrounding impingement ring 7 to hit the inner face thereof. The particles are then carried by the circulating air flow into circulation through the circulation conduit 11 and return again to the impact chamber. In this manner, the particles are repeatedly and uniformly subjected to the mechanical impact, whereby the parent particle becomes coated within a short time (from about several tens seconds to about several minutes) by a layer of child particles fused and fixed firmly to the surface of the parent particle. When the child particle has a lower melting point, it fuses only upon the impact and is fixed to the surface of the parent particle in a form of covering film.

After the above processing has been completed, the so-processed composite particulate product is discharged out of the processing apparatus by opening the valve 14 and the valve 8 (by retracting to the position shown in FIG. 1 by the dotted line). The composite particulate product is discharged within a short period of time (about several seconds) out of the impact chamber 17 and the circulation conduit 11 by the draft of the blower 24 together with the centrifugal force imparted to each particle. The discharged particles are guided to the collecting unit composed of the cyclone 20 and the bag filter 22 via the exit line 19 and are taken out of the system through the rotary valves 21 and 23. If the processing apparatus has a smaller size and the processing is not carried out in a continuous operation, the collection of the processed particulate product can be effected within a brief time only by connecting a simple bag collector directly to the exit line 19, without relying on a blower.

Using the processing apparatus explained above, four composite particulate product A, B, C and D were produced from CS, IP and PEG, in order to evaluate the properties of these products.

Production of Composite Particulate Products (1) Composite Particulate Product A Composite particulate product A was used as a comparative sample and also as an ingredient for composite particulate product B.

The surface reformation apparatus employed for the production of this composite product A was NARA Hybridization System NHS-O (of Nara Machinery Co., Ltd.) having a rotor of outer diameter of 118 mm. This apparatus is equipped with a simple bag collector connected directly to the exit line 19 as mentioned above, and no cyclone, blower and rotary valves is attached.

A powder mixture composed of 27.0 g of CS and 3.0 g of IP was charged to the processing apparatus. The particles of IP were crushed selectively in the apparatus and composite particulate product A of IP/CS was obtained, in which the surface of CS particle was coated uniformly by a layer of the finely disintegrated particles of IP fixed firmly to the CS parent particle. The circumferential velocity of the rotor was 40 m/sec and the processing time was 5 min.

(2) Composite Particulate Product B

A powder mixture composed of 16.0 g of the above composite particulate product A and 4.0 g of PEG was charged to the processing apparatus. The particles of PEG were subjected to a local fusion only upon the mechanical impact by the processing apparatus and were fused onto the parent particle of the product A to forth a fixed uniform coating layer, whereby composite particulate product B was obtained. The circumferential velocity of the rotor was 80 m/sec and the processing time was 5 min.

(3) Composite Particulate Product C

A powder mixture composed of 24.0 g of CS and 6.0 g of PEG was charged to the processing apparatus to produce preliminarily a composite particulate product (HP-1) in which the CS particle was coated uniformly with the PEG particles. A powder mixture composed of 20.6 g of HP-1 and 2.3 g of IP was charged to the processing apparatus, whereby a composite particulate product (composite particulate product C) was obtained in which the finely disintegrated particles of IP crushed selectively in the processing apparatus were not only fixed uniformly onto the surface of the PEG coating layer but also embedded therein. The circumferential velocity of the rotor was 80 m/sec and the processing time was 10 min.

(4) Composite Particulate Product D

A powder mixture composed of 18.0 g of CS, 2.0 g of IP and 4.0 g of PEG was charged to the processing apparatus to produce composite particulate product D in which a mixed phase of PEG and the finely disintegrated particles of IP crushed selectively in the apparatus was fixed over the surface of the CS parent particle. The circumferential velocity of the rotor was recorded to be 70 m/sec and the processing time was 10 min.

Typical internal structure of the composite particle for the above four products A-D is shown in FIGS. 3(A) 3(B), 3(C) and 3(D), in which the numerals 1, 2 and 3 indicate the parent particle (CS), the crystalline organic compound (IP) and the hydrophilic polisher substance (PEG), respectively.

The processing condition and the composition of the composite particulate products A-D are summarized in Table 1 below. The contents of the effective medicinal component (medicine content) in the products obtained are within a permissible range for practical use for producing medicinal preparations, though some deviations are found for different course of processing.

TABLE 1

| Processing condition | Composite particulate product | | | |
|---|---|---|---|---|
| | A | B | C | D |
| Rotor veloc.[1] (m/sec) | 40 | 80 | 80 | 70 |
| Processing time (min) | 5 | 5 | 10 | 10 |
| Temperature[2] (°C.) | 24 | 38 | 38 | 36 |
| Parent particle | CS | A | HP-1[3] | CS |
| | 27.0 g | 16.0 g | 20.6 g | 18.0 g |
| Child particle | IP | PEG | IP | IP |
| | 3.0 g | 4.0 g | 2.3 g | 2.0 g |
| | | | | PEG |
| | | | | 4.0 g |

TABLE 1-continued

| Processing condition | Composite particulate product | | | |
|---|---|---|---|---|
| | A | B | C | D |
| Medicine content (%) | 8.61 | 5.89 | 9.11 | 6.71 |

Note
[1] Circumferential velocity of rotor
[2] The highest temperature of the circulating gas
[3] A product from CS 24 g and PEG 6 g (60 m/sec, 5 min., highest gas temp. = 25° C.)

Evaluation of Composite Particulate Products

(1) Observation by Electron Microscope

Figure 4:
FIG. 4, Product (A) and Product (D) show a set of scanning electron microscopic photographs of a typical composite particle according to the present invention (D) and of a typical composite particle of conventional technique (A) both immediately after the preparation.
Figure 4:
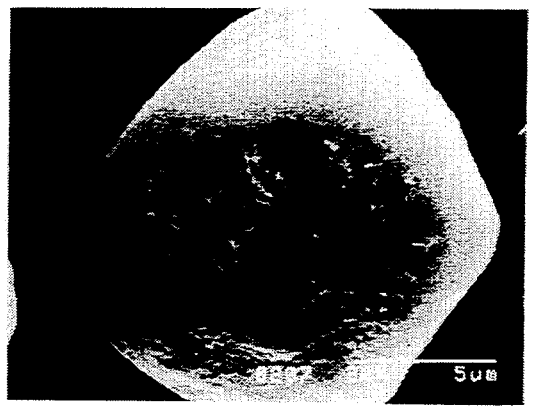
Figure 5:
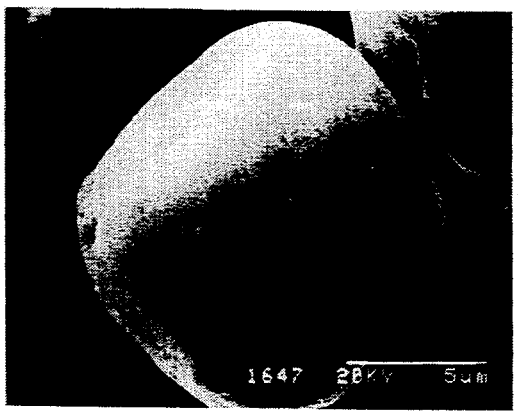
FIG. 5, Product (A) and Product (D) show another set of scanning electron microscopic photographs for the composite particles corresponding to FIGS. 4, Product (A) and Product (D), after about 240 days from preparation.
Figure 5:
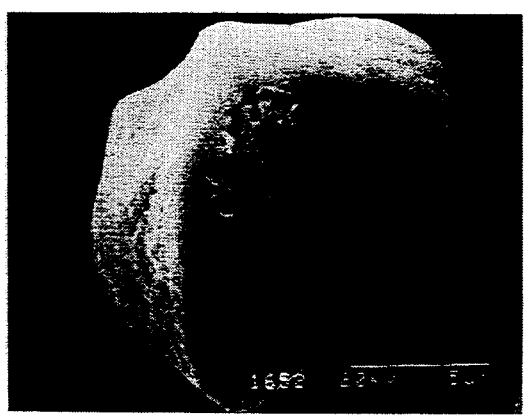

The surface conditions of the composite particulate products were observed by a scanning electron microscope (S-530 of Hitachi Ltd.) after the particle was plated with gold. FIGS. 4, Product (A) and Product (D) includes two scanning electron microscopic photographs showing the surface condition of each typical particle of composite particulate product A (comparative sample) and composite particulate product D both directly after their production. FIG. 5, Product (A) and Product (D) include also two scanning electron microscopic photographs similar to FIG. 4, Product (A) and Product (D) but after about 240 days from their production.

As seen in FIG. 4, Product (A), and Product (D) in the particle of product A, the CS parent particle was coated by a smooth laminar fixed cover layer of IP. In contrast thereto, as for the particle of product D, the surface of the CS parent particle was coated by a mixed phase of IP and PEG, in which a crystalline PEG was observed in a part of the coating layer. Also the particles of other composite products had shown a similar appearance in the scanning electron microscope inspection.

In FIG. 5, Product (A) and Product (D) similar surface conditions were observed, while no temporal variation of the surface condition was seen.

(2) Evaluation by Differential Scanning Calorimetry

Each sample of the composite particulate products in an amount of 10-15 mg was placed in an aluminum pan for measurement and examined on a differential scanning calorimeter (MTC 1000 & DSC 3100 of the firm Mack Science Kabushiki Kaisha) at a temperature elevation rate of 10° C. per minute. The results of the calorimetric analysis of the samples of composite particulate products A-D directly after their production and of a simple binary physical mixture of CS and IP and of a simple tertiary physical mixture of CS, IP and PEG are summarily recited in FIG. 6. The change in the result of differential scanning calorimetry for the composite particulate product B in the course of storage is shown in FIG. 7.

Figure 6:
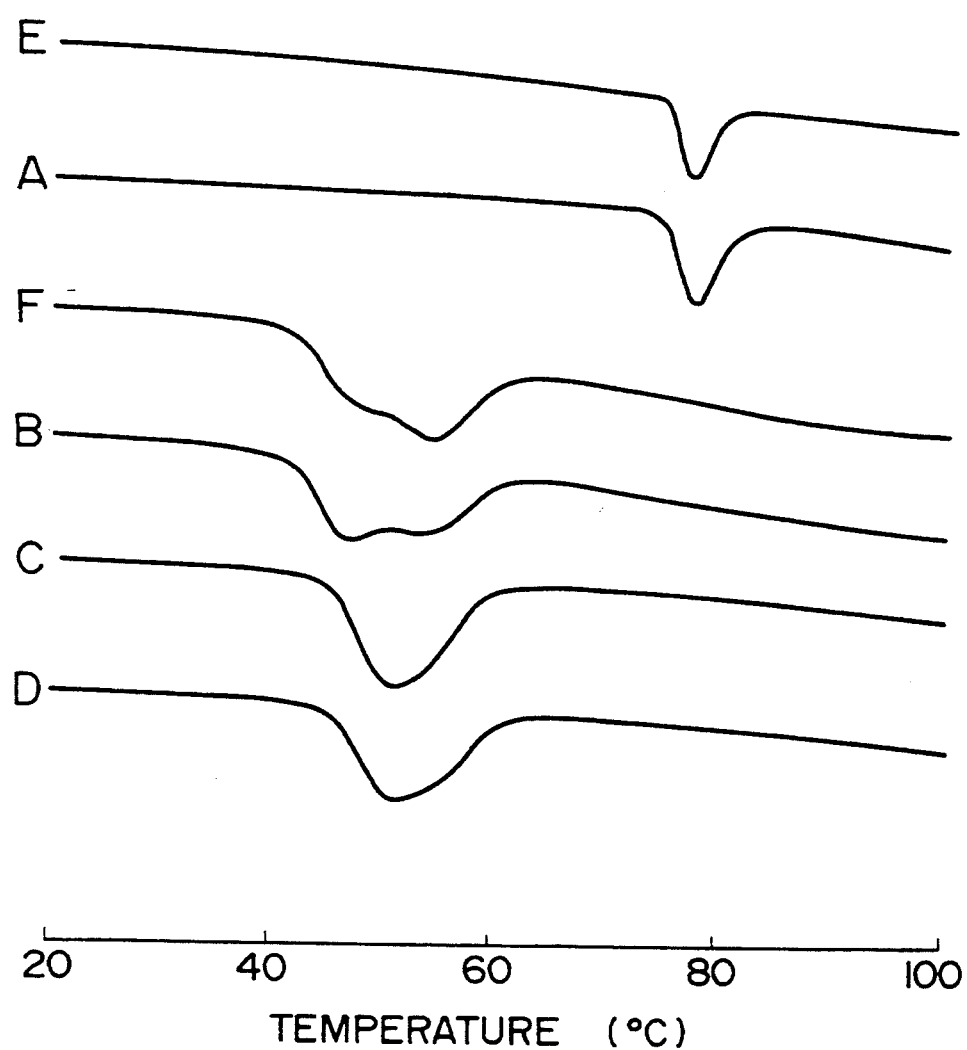
FIG. 6 shows the curves in the charts of differential scanning calorimetry for the composite particulate products as given in Examples each immediately after the preparation.
Figure 7:
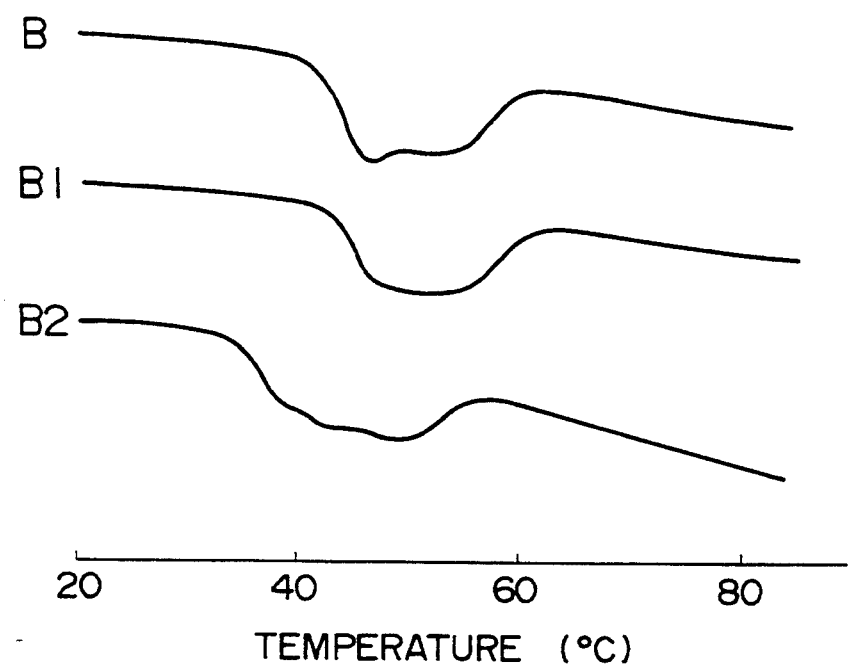
FIG. 7 shows the change of the curve in the chart of differential scanning calorimetry for a composite particulate product with time: (B) immediately after preparation, (B1) 30 days after preparation, and (B2) 238 days after preparation.

FIG. 6 shows that the simple binary physical mixture E composed of CS and IP and the composite particulate product A (comparative sample) revealed both an endothermic peak at around 74° C. due to the melting of IP, while no corresponding endothermic peak is found for all the other samples containing PEG inclusive of that of the simple tertiary physical mixture F composed of CS, IP and PEG. However, the simple tertiary physical mixture F revealed two endothermic peaks at around 45° C. and around 55° C. This may presumably be due to the fact that PEG having a melting point lower than that of IP will melt first in the course of temperature elevation and IP particles will be dissolved in this molten PEG and, thus the intrinsic endothermic peak of IP disappears.

The sample of composite particulate product B reveals also two endothermic peaks as in the physical mixture F. This may be due to the fact that the CS parent particle is first covered by a fixed layer of IP and thereon is further coated by a layer of PEG and, thus two separate layers are laminated, so that the solid solution will be formed only at the interface between these two layers only to a scarce extent, whereby its thermal behavior does not substantially differ from that of the physical mixture.

On the other hand, the composite particulate products C and D revealed only one endothermic peak, which may be due to that the proportion of the formed solid solution of PEG is greater than that of composite particulate product B.

In the case of composite particulate product D, the CS parent particle is coated by a fixed layer formed from PEG and IP simultaneously, so that the mixing of these component is better, while however, a sufficient transference of impact to the IP particles will not be attained by the presence of PEG particles. In the case of composite particulate product C, the CS parent particle is preliminarily coated by a layer of PEG and thereon is further coated by a layer of IP particles, so that the IP particles will be subjected to an intensive impact without being hindered by the PEG particles, whereby they are forced to intrude into the layer of PEG by the impact, while being finely disintegrated. Therefore, the proportion of solid solution formed is higher for the composite particulate product C than for the product D.

FIG. 7 shows the behavior in the differential thermal analysis for composite particulate product B in the course of storage after its production, in which curve B represents the differential calorimetric analysis curve directly after the production thereof, curve B1 is that determined after 30 days from its production and curve B2 is that determined after 238 days from its production.

(3) Evaluation by Powder X-Ray Diffractometry

Each sample was examined by powder X-ray diffractometer MXP³ System of Mack Science Kabushiki Kaisha with CuK α-rays. The proportion of the medicinal component existing in crystalline state was determined using a calibration curve prepared preliminarily with several physical mixtures having different content of the crystalline medicinal component. Here, lithium fluoride was employed as the standard and the determination was effected by an internal standard method.

Figure 8:
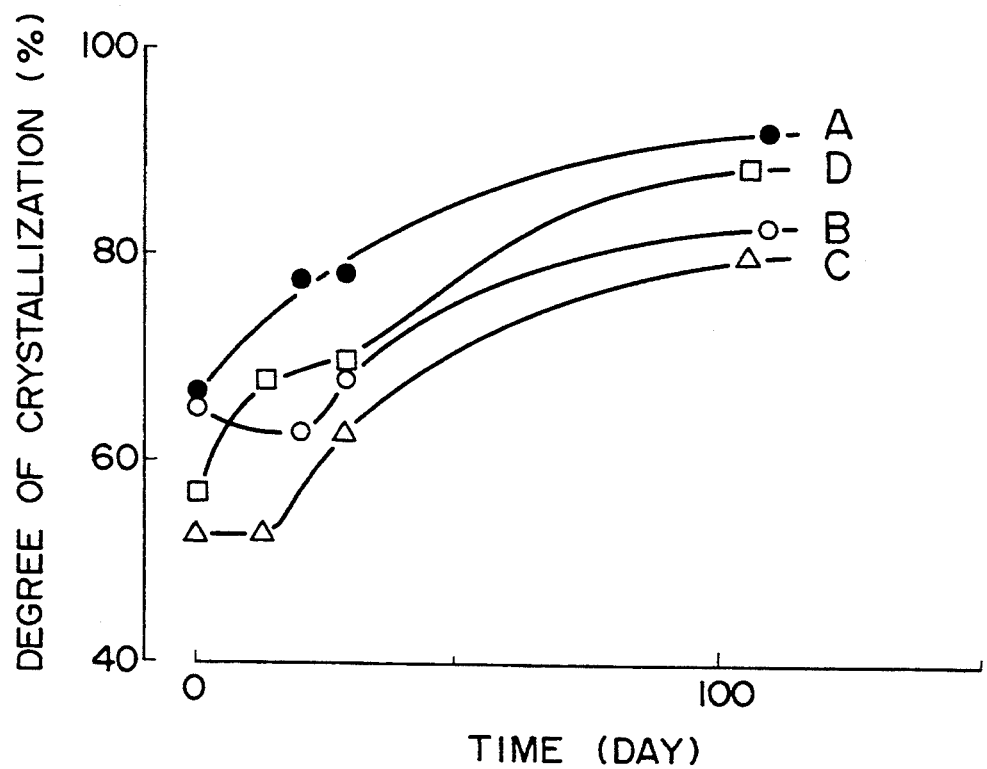
FIG. 8 is a graph showing the temporal change of the proportion of the medicinal component which is in the crystalline state with respect to the total amount of the medicinal component for composite particulate products (A), (B), (C), and (D) as determined by X-ray powder diffractometry.

The change in the proportion of the medicinal component in crystalline state was determined by powder X-ray diffractometry in the course of storage and is shown in FIG. 8. The degree of crystallization in FIG. 8 represents a proportion of medicinal component in crystalline state relative to the total amount of the medicinal component in the composite particulate product. As seen, the proportion of the medicinal component in crystalline state (degree of crystallization) in composite particulate product A (comparative sample) increased in the course of storage and has reached at a constant value (93%) after about 100 days from its production. Composite product C showed also a similar variation as product A, while it showed a lower value for each determination than that of product A and has reached to a constant value (80%) which is lower than that of product A. The proportions of the medicinal component in crystalline state for composite particulate products B and D were found to lie between the values for products A and C.

From the above, it is recognizable that IP is subjected to a selective crushing by the action of striking impact and the so crushed particles are fixed on the CS parent particle, wherein a part of them are converted into noncrystalline state. It was observed that there were cases in which solid solution was formed from IP with PEG and in which no such solid solution was formed. The portion of IP fixed onto the CS parent particle in a noncrystalline state but not forming a solid solution will recrystallize after some time has elapsed. Therefore, the larger the proportion of the solid solution in PEG, the larger will be the proportion of IP held in the noncrystalline state.

As explained above in detail, it has now become possible according to the present invention to increase the proportion of amorphous portion of crystalline organic compound by fixing the crystalline organic compound and a hydrophilic polymer compound on the surface of a core particle by means of impact application in a high velocity gas stream and suppress the recrystallization thereof.

According to the present invention, it is also made possible to maintain a stable composite state of the crystalline organic compound with the core particle.

Moreover, due to the dry processing system according to the present invention, which does not employ any solvent, a considerable reduction of the production cost for composite particulate products is attained, while producing a large amount of composite particulate product efficiently within a short period of time.

In this manner, it is made possible by the method according to the present invention to obtain medicinal preparations exhibiting higher performance and superior quality.

I claim:

1. A method of making a crystalline organic compound amorphous by mechanical impact means, comprising the step of repeatedly imposing mechanical impacts on a core particle, the crystalline organic compound and a hydrophilic polymer in recycled high-velocity gas streams, thereby forming a solid-solid solution of said hydrophilic polymer dispersed and mixed in said crystalline organic compound on the surface of said core particle so as to make said crystalline organic compound amorphous and to prevent recrystallization thereof.

2. The method of claim 5, wherein the crystalline organic compound is first fixed onto the surface of core particles, and the hydrophilic polymer compound is then fixed onto a surface of the crystalline organic compound.

3. The method of claim 5, wherein the hydrophilic polymer compound is first fixed onto a surface of core particles, and then the crystalline organic compound is fixed onto a surface and inside of the hydrophilic polymer compound.

4. The method of claim 5, wherein the crystalline organic compound and the hydrophilic polymer compound are simultaneously fixed onto a surface of core particles.

5. The method of claim 1 wherein said hydrophilic polymer easily forms a solid-solid solution with the organic compound but does not easily form a solid-solid solution with the core particle.

6. The method of claim 5 wherein said hydrophilic polymer is selected from the group consisting of polyethylene glycol, polyvinyl pyrrolidone, gelatine, hydroxypropyl cellulose and polyacrylamide.

7. The method of claim 1 wherein said core particles are spherical or elliptical in shape.

8. The method of claim 1 wherein said core particles have diameters in the range from about 0.5 micrometers to about 1 mm.

9. The method of claim 8 wherein said core particles are selected from the group consisting of: crystalline cellulose, hydroxypropyl cellulose, carboxymethyl cellulose and derivatives thereof; starch and derivatives thereof; sugars, synthetic high polymeric materials and powders of metals.

10. The method of claim 1 wherein mechanical impact members are rapidly rotated in a substantially enclosed chamber so as to create said high-velocity gas streams.

11. The method of claim 10 wherein said mechanical impact members reach a circumferential velocity in use which is between about 30 to about 150 meters/second.

12. A method of forming a solid pharmaceutical composition which is readily soluble in a diluent such as water comprising the step of combining a pharmaceutically active crystalline organic compound, a hydrophilic polymer and a core particle in a mixing chamber to form a mixture by a dry process and repeatedly imposing mechanical impacts on the mixture in high velocity gas streams thereby forming a solid-solid mixture of the hydrophilic polymer and the crystalline organic compound on the surface of the core particle, wherein the method makes the crystalline organic compound amorphous and prevents re-crystallization thereof in the pharmaceutical composition formed by the method.

13. The method of claim 12 wherein said pharmaceutically active compound is selected from the group consisting of ibuprofen, ketoprofen, flurbiprofen, indomethacin, phenacetin, oxyphenbutazone, ethenzamide, salicylamide, salicylic acid and benzoic acid.

14. The method of claim 12 wherein the pharmaceutical compound is ibuprofen, the hydrophilic polymer is polyethylene glycol and the core particle is formed from corn starch.

* * * * *